(12) United States Patent
Kroner

(10) Patent No.: US 8,765,753 B2
(45) Date of Patent: Jul. 1, 2014

(54) PROCESS FOR THE PREPARATION OF S-TRIAZINE COMPOUNDS

(75) Inventor: Rudi Kroner, Weisenheim am Sand (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/004,180

(22) PCT Filed: Mar. 21, 2012

(86) PCT No.: PCT/IB2012/051344
§ 371 (c)(1),
(2), (4) Date: Sep. 10, 2013

(87) PCT Pub. No.: WO2012/127425
PCT Pub. Date: Sep. 27, 2012

(65) Prior Publication Data
US 2014/0005387 A1 Jan. 2, 2014

Related U.S. Application Data

(60) Provisional application No. 61/466,481, filed on Mar. 23, 2011.

(30) Foreign Application Priority Data

Mar. 23, 2011 (EP) ..................................... 11159352

(51) Int. Cl.
*A01N 43/66* (2006.01)
(52) U.S. Cl.
USPC ........................................................ 514/241
(58) Field of Classification Search
USPC ........................................................ 514/241
See application file for complete search history.

(56) References Cited

U.S. PATENT DOCUMENTS

| 4,617,390 A | 10/1986 | Hoppe et al. |
| 4,656,272 A | 4/1987 | Martin et al. |
| 2011/0041471 A1 | 2/2011 | Sebastian et al. |

FOREIGN PATENT DOCUMENTS

CN 101896657 A 11/2010

OTHER PUBLICATIONS

Andrea et al., Photochemistry and Photobiology, Jul. 2005, vol. 81, No. 4, pp. 949-952.

*Primary Examiner* — Jeffrey H Murray
*Assistant Examiner* — Oluwafemi Masha
(74) *Attorney, Agent, or Firm* — Shiela A. Loggins

(57) ABSTRACT

A process is described for the preparation of s-triazine derivatives of the formula in which R is a $C_1$-$C_{12}$-alkyl radical, by reacting a cyanuric acid halide with a p-aminobenzoic acid ester, which comprises a $C_6$-$C_{12}$-alkyl radical as radical of the ester alcohol, in a molar ratio of 1:3 to 1:5 in a xylene isomer mixture as solvent. 10 The process is characterized in that the solvent is used in amounts of from 0.6 to 2.1 mol/l.

(1)

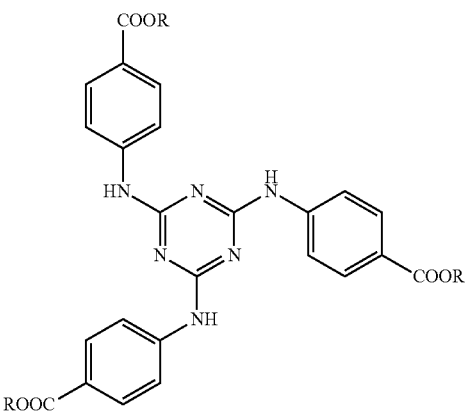

9 Claims, 1 Drawing Sheet

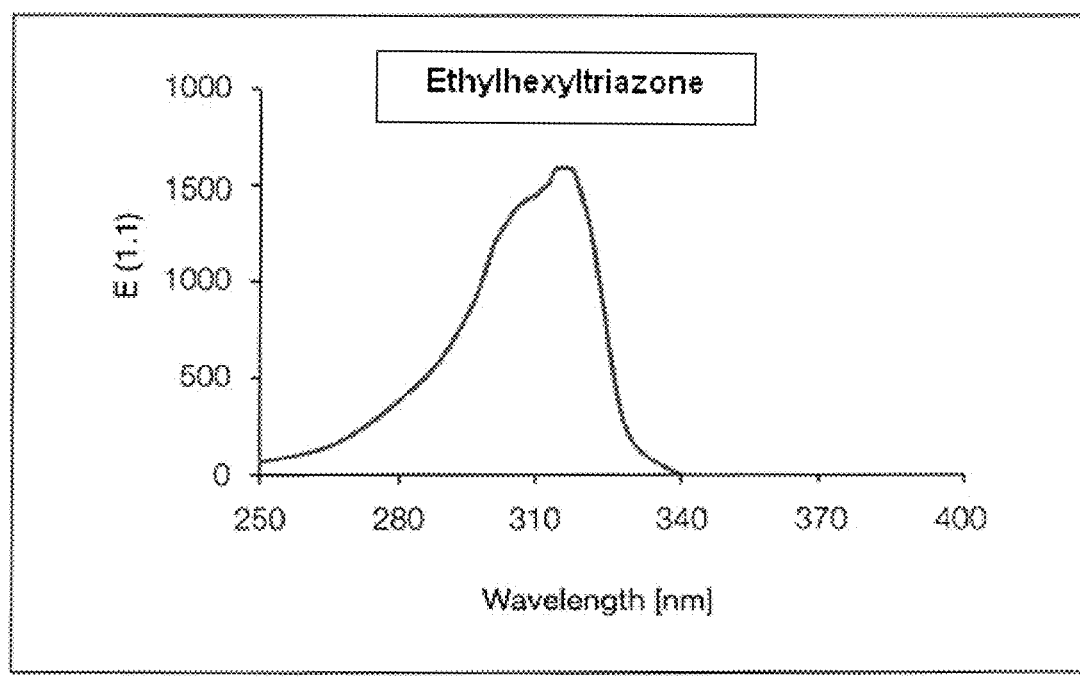
E (1.1) > 1500; λ$_{max}$ = 314 nm

PROCESS FOR THE PREPARATION OF S-TRIAZINE COMPOUNDS

This application is a national stage of PCT/IB2012/051344, filed Mar. 21, 2012, the contents of which is herein incorporated entirely by reference.

DESCRIPTION

The present invention relates to a process for the technically simple and economic preparation of s-triazine compounds, which can be used as photoprotective agents.

DE-A 32 05 398 describes s-triazine derivatives which are substituted by radicals of p-aminobenzoic acid esters, which are extraordinarily good photoprotective agents. According to the preparation examples, the compounds are prepared by reacting cyanuric chloride with a p-aminobenzoic acid ester in relatively large amounts of an aliphatic or aromatic hydrocarbon, in particular benzine or xylene, as solvent. The solvent residues remaining in the end product of ca. 20 to 30% by weight have to be completely removed by careful drying under reduced pressure.

This drying and the solvent exchange on an industrial scale cost energy and are very time-consuming since if the compounds are dried too rapidly at excessively high temperatures, the pure product that is produced has a lower solubility in the oils usually used in cosmetics.

Surprisingly, it has now been found that by using significantly reduced amounts of solvents, products of high purity and large yield can be prepared.

The present invention therefore relates to a process for the preparation of s-triazine derivatives of the formula

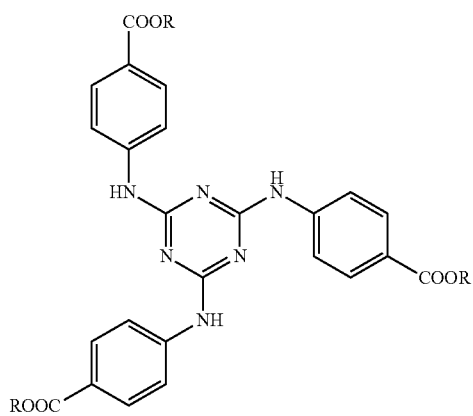

(1)

in which
R is a $C_1$-$C_{12}$-alkyl radical,
by reacting a cyanuric acid halide with a p-aminobenzoic acid ester, which comprises a $C_1$-$C_{12}$-alkyl radical as radical of the ester alcohol, in a molar ratio of 1:3 to 1:5 in a xylene isomer mixture as solvent, characterized in that the solvent is used in amounts of from 0.6 to 2.1 mol/l.

FIG. 1—Absorption spectrum for ethylhexyltriazone (CAS No. 88122-99-0).

Starting compounds for the preparation of the s-triazine derivatives according to the invention are, besides cyanuric chloride or bromide, preferably cyanuric chloride, the $C_1$-$C_{12}$-n- or isoalkyl esters of p-aminobenzoic acid, preferably the $C_6$-$C_{10}$-n- or isoalkyl esters and very particularly preferably the 2-ethylhexyl ester (=ethylhexyltriazone).

Preferably, the process according to the invention relates to the preparation of the compound of the formula

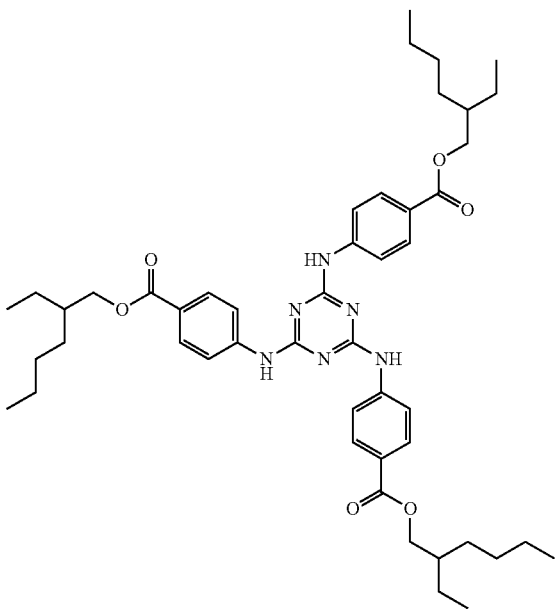 [SMILES: CCCCC(CC)COC(=O)c1ccc(Nc2nc(Nc3ccc(C(=O)OCC(CC)CCCC)cc3)nc(Nc3ccc(C(=O)OCC(CC)CCCC)cc3)n2)cc1]

(INCI name: Ethylhexyl Triazone).

The xylene isomer mixture is recycled in the course of the process. By reducing the amount of solvent, less water and fewer other secondary components are therefore entrained. The energy and time requirements decrease; the mixture is altogether more concentrated.

In a particularly preferred embodiment, the reaction is carried out without solvents.

Preferably, the reaction is carried out at a temperature of 85-140°, preferably 105-125°, particularly preferably 110-120° C. The reaction can be carried out in this temperature range as a quasi one-stage reaction. Surprisingly, it has been found that during a reaction carried out within this temperature range, the formation of monohydroxytriazine, a secondary component, which is extremely troublesome in comparatively small amounts and reduces the yield, decreases significantly.

In a preferred embodiment, p-aminobenzoic acid ester is dosed stoichiometrically. Besides the increased number of possibilities for use (the p-aminobenzoic acid ester, in the event of excess, is discharged after the reaction via the bottom during the ethanol recovery), the product quality is positively influenced since secondary components are entrained as a function of concentration and temperature during the crystallization. Additionally, the end temperature of the process of ca. 20-25° C. can be fallen below, i.e. it is possible to cool to lower temperatures, which leads to an improved yield.

Preferably, the p-aminobenzoic acid ester is purified by vacuum distillation prior to dosing.

The xylene isomer mixture used as reaction solvent is preferably azeotropically dewatered prior to the reaction.

In a further preferred embodiment, the cyanuric acid halide is introduced as initial charge as suspension with the azeotropically dewatered xylene isomer mixture. For this, the solvent is preferably transferred to the receiver at elevated temperature, in particular at a temperature of from 80 to 90° C., in order to prevent the possible formation of monohydroxytriazine upon adding the cyanuric acid halide for the preparation of the suspension at a temperature of >60°.

In the case of the conversion reactions of cyanuric acid halide known hitherto, problems have always arisen with caked cyanuric acid halide on the walls of the reaction vessels. As a result, the feed amounts of cyanuric acid halide fluctuated considerably, and an excess of the p-aminobenzoic acid ester was required to ensure the complete conversion of cyanuric acid halide.

In order to overcome this disadvantage, in the present process, use is preferably made of rotating cleaning nozzles which are operated with the process solvent under pressure in order to remove any adhesions of cyanuric acid halide present in the receiver container and in the feed tube for solid cyanuric acid halide. This permits a precise and virtually stoichiometric dosing of the p-aminobenzoic acid ester.

A particular embodiment of the process according to the invention consists in introducing the p-aminobenzoic acid ester purified by vacuum distillation into the reactor which comprises the dewatered xylene isomer mixture and heating it to ca. 80-110° C., preferably 85-95° C., and then metering in the cyanuric acid halide suspension at a temperature of 110-120° C.

When the cyanuric acid halide dosing is complete, heating is carried out with a ramp to 105-125° C., preferably 110-120° C. The post-reaction is carried out at a temperature of 105-125° C., preferably 115-120° C. from a receiver for 1-5 h, preferably 1.5-2.5 h.

The reaction mixture is then cooled, and neutralized with a base, for example $NH_3$, alkali metal hydroxide, carbonate or bicarbonate. The process solvent is distilled off, replaced by another solvent, for example an alcohol, and filtered. The mixture is then precipitated by chilled crystallization, and filtered and the product is washed and dried.

The sliding ring liquid used in the dryer is preferably 3% strength hydrogen peroxide solution. This can avoid problems with germs. Small amounts of the sliding ring liquid can find their way into the product; however, this has proven unproblematical since the hydrogen peroxide decomposes to harmless components which are removed during drying.

As a result of the fact that the p-aminobenzoic acid ester is dosed stoichiometrically in the process according to the invention, there is a lack of an excess of p-aminobenzoic acid ester in the reaction mixture which can be used as solvent for the column bottom of the distillation column and also for the distillation residue.

According to the invention, palatinol (phthalic acid ester) and/or 2-ethylhexylhexanol can perform this function.

The compounds of the formula (1) prepared by the process according to the invention are suitable as photoprotective agents in cosmetic preparations. Examples of the compositions of such cosmetic preparations as photoprotective emulsions, oil-in-water photoprotective creams, water-in-oil photoprotective creams or photoprotective foams can be found in EP 0 087 098.

Customary cosmetic oils serving as solvents for compounds of the formula (1) in cosmetic preparations are, besides the parent $C_6$-$C_{10}$-alkanoic acid $C_{10}$-$C_{20}$-alkyl esters such as cetylstearyl 2-ethylhexanoate, described in DE 35 18 670, for example peanut oil, olive oil, isopropyl stearate, isopropyl myristate, coconut fatty acid triglycerides, caprylic/capric triglyceride, triethyl citrate, polyethylene glycol glyceryl cocoate, diisopropyl adipate, propoxylated myristyl alcohol or mixtures thereof. The solubility of the compound of the formula (1) in the specified cosmetic oils is sufficiently high.

The examples below illustrate the invention without limiting it to these.

EXAMPLES

Example 1

Preparation of Ethylhexyltriazones

Structural Formula:

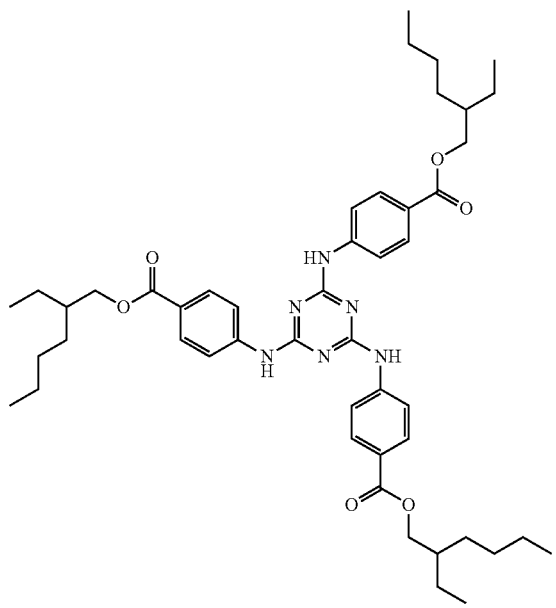 [SMILES: CCCCC(CC)COC(=O)c1ccc(Nc2nc(Nc3ccc(C(=O)OCC(CC)CCCC)cc3)nc(Nc3ccc(C(=O)OCC(CC)CCCC)cc3)n2)cc1]

500 kg of cyanuric chloride are suspended with stirring in a receiver in 1000 l of xylene at elevated temperature (>60° C.). Towards the end of the reaction, ca. 50 l of xylene are metered into the receiver via a rinsing nozzle in order to rinse any adhering cyanuric chloride from the wall etc. into the suspension.

In the reactor, 2000 l of xylene are introduced as initial charge beforehand and dewatered by azeotropic distillation (desired value: <250 ppm, determined by Karl-Fischer titration). After checking the water content, 1000 l of the xylene are transferred to the receiver and used for the suspension of the xylene. The transfer preferably takes place at temperatures of 60-80° C.

Then, ca. 2020 kg of 2-ethylhexyl p-aminobenzoate, which has been purified beforehand by distillation, are pumped into the xylene in the reactor and heated to ca. 90° C. Over the course of 3 h, the contents are then metered into the receiver in a temperature-controlled manner (evolution of HCl), during which the temperature is kept at 105-120° C. By introducing $N_2$, HCl is stripped out of the reaction mixture as far as possible.

The post-reaction takes place at 110-120° C. for 1 h.

Example 2

Laboratory Example

In a 750 ml flask, 147 g of ethylhexyl p-aminobenzoate are introduced as initial charge with 75 ml of xylene and heated to 120° C. Over the course of one hour, 37.5 g of cyanuric chloride are metered in with stirring at 115°-125° C. and subsequently rinsed with 37 ml of xylene. At ca. 120° C., the post-reaction takes place over the course of 1 h. After cooling to ca. 90° C., the mixture is neutralized with sodium chloride solution and subsequently stirred for 30 minutes.

The organic phase is separated off and analysed by means of HPLC. 90.5 area % main component, 0.5% by weight of secondary components.

The resulting ethylhexyltriazone (CAS No. 88122-99-0) exhibits an absorption spectrum as in FIG. 1.

The invention claimed is:

1. A process for the preparation of s-triazine derivatives of the formula

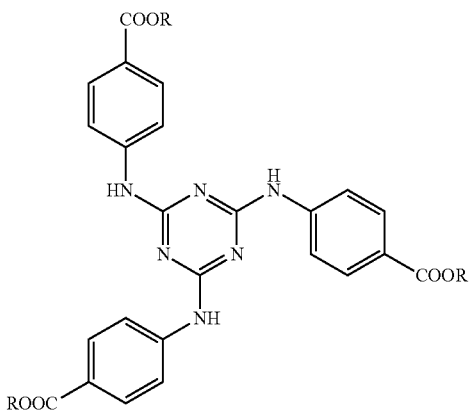

(1)

in which
R is a $C_1$-$C_{12}$-alkyl radical,
by reacting a cyanuric acid halide with a p-aminobenzoic acid ester, which comprises a $C_6$-$C_{12}$-alkyl radical as radical of the ester alcohol, in a molar ratio of 1:3 to 1:5 in a xylene isomer mixture as solvent, characterized in that the solvent is used in amounts of from 0.6 to 2.1 mol/l.

2. The process according to claim 1, characterized in that the s-triazine is a compound of the formula

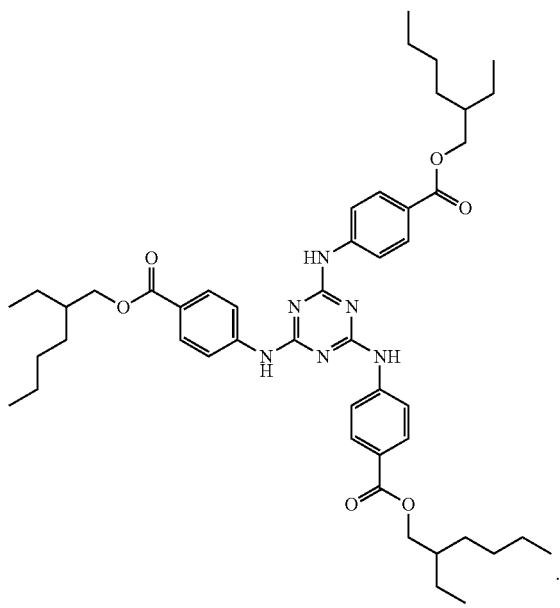 [SMILES: CCCCC(CC)COC(=O)c1ccc(Nc2nc(Nc3ccc(C(=O)OCC(CC)CCCC)cc3)nc(Nc3ccc(C(=O)OCC(CC)CCCC)cc3)n2)cc1]

.

3. The process according to claim 1, characterized in that the xylene isomer mixture is azeotropically dewatered prior to the start of the reaction.

4. The process for the preparation of s-triazine derivatives of the formula

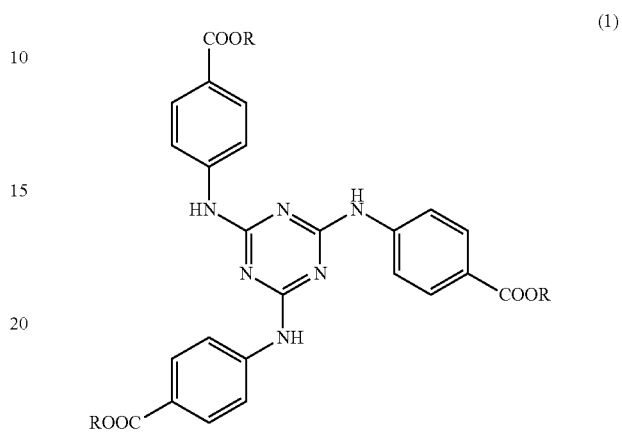

(1)

in which
R is a $C_1$-$C_{12}$-alkyl radical,
by reacting a cyanuric acid halide with a p-aminobenzoic acid ester, which comprises a $C_6$-$C_{12}$-alkyl radical as radical of the ester alcohol, in a molar ratio of 1:3 to 1:5, characterized in that the reaction is carried out without solvents.

5. The process according to claim 1, characterized in that the reaction is carried out at a temperature of 85-140° C.

6. The process according to claim 1, characterized in that the p-aminobenzoic acid ester is dosed stoichiometrically.

7. The process according to claim 1, characterized in that the cyanuric acid halide is used as suspension with the azeotropically dewatered xylene isomer mixture.

8. The process according to claim 7, characterized in that cyanuric acid halide adhering to the reaction vessel is removed using rotating cleaning nozzles which are operated with the solvent under pressure.

9. The process according to claim 1, characterized in that the p-aminobenzoic acid ester purified by vacuum distillation is introduced into the reactor which comprises the dewatered xylene isomer mixture and heated to 80-110° C., and then the cyanuric acid halide suspension is metered in at a temperature of 110-120° C.

* * * * *